US006526969B2

(12) United States Patent
Nilsson et al.

(10) Patent No.: US 6,526,969 B2
(45) Date of Patent: Mar. 4, 2003

(54) METHOD AND DEVICE FOR RELEASING POWDER

(75) Inventors: Lars-Gunnar Nilsson, Köping (SE); Thomas Nilsson, Mariefred (SE)

(73) Assignee: Microdrug AG, Hergiswil NW (CH)

( * ) Notice: Subject to any disclaimer, the term of this patent is extended or adjusted under 35 U.S.C. 154(b) by 0 days.

(21) Appl. No.: 09/875,048

(22) Filed: Jun. 7, 2001

(65) Prior Publication Data

US 2002/0144680 A1 Oct. 10, 2002

(30) Foreign Application Priority Data

Apr. 5, 2001 (SE) .............................................. 0101233

(51) Int. Cl.[7] ........................ A61M 15/00; A61M 16/10

(52) U.S. Cl. ............................ 128/203.15; 128/204.12; 128/204.13; 128/204.11; 128/202.21; 128/203.23; 128/203.24

(58) Field of Search ....................... 128/203.15, 203.12, 128/204.13, 204.11, 202.21, 203.23, 203.29, 203.19, 203.24

(56) References Cited

U.S. PATENT DOCUMENTS 5,388,572 A * 2/1995 Mulhauser et al. .... 128/203.15
5,394,868 A * 3/1995 Ambrosio et al. ..... 128/203.15
5,460,173 A * 10/1995 Mulhauser et al. .... 128/203.15
6,092,522 A * 7/2000 Calvert et al. ......... 128/203.21
6,240,918 B1 * 6/2001 Ambrosio et al. ..... 128/203.15
6,336,455 B1 * 1/2002 Howlett ................. 128/203.15
2001/0010224 A1 * 8/2001 Gonda et al. .......... 128/200.14

* cited by examiner

*Primary Examiner*—William C. Doerrler
*Assistant Examiner*—Mark Shulman
(74) *Attorney, Agent, or Firm*—Young & Thompson

(57) ABSTRACT

An inhaler device and a method in which powder for inhalation is jetted off a prepared device surface containing a defined pre-metered quantity of finely divided powder. The jetting function is obtained by a directed air stream pushing or cutting free a medical powder applied to a carrier surface and by creating a stream of air dispersing the powder into inspiratory air at the moment it is being inhaled. The inhaler device includes active (air permeable) porous walls for preventing finely divided powder from sticking to the inner faces of the inhaler device by creating a pressure gradient across the active wall, thus forcing a small flow of air through the active wall thereby keeping the powder from sticking to the inner faces.

12 Claims, 6 Drawing Sheets

METHOD AND DEVICE FOR RELEASING POWDER

TECHNICAL FIELD

The present invention relates to a method and a device for releasing a finely divided powder to be inhaled and more particularly a method and a device for releasing a medical powder from a dosing carrier connected to an inhaler for creating a well defined and efficiently inhaled medication dose.

BACKGROUND

Today supply and distribution of medical powders take place in many different ways. Within health care there is rapidly growing interest in the possibility to dose and distribute powder directly to the lungs of a patient by means of an inhaler to obtain an efficient, fast, and patient friendly administration of the specific medical substance.

In order to make certain that the medical powder to be administered will be safely carried to the lungs of a patient, the powder should have a grain size less than 5 μm. Large grain sizes generally will stick in the oral cavity and the throat, and too small grain sizes may follow the expiration air out.

However, powder having a small grain size will demonstrate a strong tendency to agglomerate, i.e. to clod into larger grains. In the inhalers being used today a large portion of the powder is agglomerated when it is dosed and much powder therefore will stick to the upper respiratory tracts. Different manners to de-agglomerate the powder have been developed and in most of the cases, inspiration air is used to disassemble the agglomerated powder. Another method where de-agglomeration is performed by mechanical means is disclosed in for instance the granted Swedish Patent Application No. 9802648-7 (Swedish publication SE 512 433).

It is also common to utilize carriers having a larger grain size onto which the fine powder is distributed. Upon inspiration the large size grains will then stick in the oral cavity while the small grains will be let free and proceed to the lung. Some manufacturers also utilize electrically driven propellers, piezo-vibrators and/or mechanical vibration to disassemble the agglomerates. To obtain a large portion of separate small particles in the inspiration air is thus a very important factor to achieve a high efficiency upon inhalation.

One of the problems upon inhalation of a medical powder is that a relatively large portion of the dose will also stick in the inhaler device. To be able to include all powder and disassemble agglomerates a high air velocity is needed. However, the high velocity also has a negative influence on the emitted dose, as a large portion of the powder will stick to the walls within the inhaler. A dose given by an inhaler of today the respiratory part (grain size less than 5 μm) may often be only 20% of the dose.

The problems are illustrated in U.S. Pat. No. 5,740,794 and WO 96/09085, for example, where an apparatus and a method are demonstrated for aerosolizing a medicament dose comprising dry powder to be suitable for inhalation. The applied method relies on the use of pressurized gas, normally air, for dispersing and transporting the powder and separating agglomerates into individual powder particles in the dose by using high air speeds in certain parts of the transport tube system, thereby de-agglomerating by introducing very high shear forces. Besides the inconvenience of relying on an external source of pressurized air, the evidence is far from conclusive regarding the powder retention in the powder receptacle and the transport tube system.

In order to be able to use inhalation to provide administration and in this manner replace injection of medicine the grain size must be very small. For an optimal amount of substance to reach the alveoli, an administered powder dose should preferably have an aerodynamic grain size less than 3 μm. Besides, the inspiration must be carried out in a calm way to decrease air speed and thereby depositions in the upper respiratory tracts.

For achieving a high respiratory dose a so-called spacer is often used to have the small grains evenly distributed in a container from which the inhalation can take place. In principle a dosing device or an inhaler is coupled to a container having a relatively large volume and into this container a powder or an aerosol is injected, which partly is distributed in the air space and partly sticks to the walls. Upon inhalation from the spacer the fine powder floating free in the air will effectively reach the alveoli. This method in principle has two drawbacks, firstly difficulties to control the amount of medicine emitted to the lung as an uncontrolled amount of powder sticks to the walls of the spacer and secondly difficulties in handling the relatively space demanding apparatus. It has been demonstrated, e.g. in U.S. Pat. No. 5,997,848 that systemic delivery of dry insulin powder can be accomplished by oral inhalation and that the powder can be rapidly absorbed through the alveolar regions of the lungs. However, dose resolution still seems to be low. According to the disclosure, the insulin doses have a total weight from a lowest value of 0.5 mg up to 10–15 mg of insulin and the insulin is present in the individual particles at from only 5% up to 99% by weight with an average size of the particles below 10 μm.

However, there is still a demand for a method and a device simplifying administration of medical powder by means of an inhaler device providing a compact arrangement without the need of, for instance, a space-demanding spacer or external power sources.

SUMMARY

The present invention discloses a method and a device for efficiently obtaining by inhalation a total amount of administered medical powder spatially distributed in the inspiration air, preferably without the use of a so-called spacer.

According to the present method the powder is jetted off a prepared device surface containing a defined pre-metered quantity of finely divided powder, preferably an electro-powder constituting an electro-dose. The jetting function is normally the result of the inhalation effort on the user's behalf, but in some cases the effort is aided by internal or external sources of power. By way of a user-actuated release mechanism, a directed air stream, having the characteristic of an air jet, pushes or cuts free a medical powder deposited on the surface of a carrier member. The stream of air disperses the powder and floats the individual particles into the air just as it is being inhaled. An inhaler device utilizing the present method is preferably further provided with active (air permeable) porous wall elements for further preventing powder grains from sticking to the inside faces of the inhaler device. The inhalation effort of the user creates a total pressure gradient preferably in the range 1–5 kPa over the inhaler. A part of the pressure drop is available over the active wall, thus forcing a flow of air through the active wall such that the resulting airflow prevents the floating powder particles from touching the inside faces.

BRIEF DESCRIPTION OF THE DRAWINGS

The invention, together with further objects and advantages thereof, may best be understood by referring to the following description taken together with the accompanying drawings, in which.

DETAILED DESCRIPTION

Figure 1:
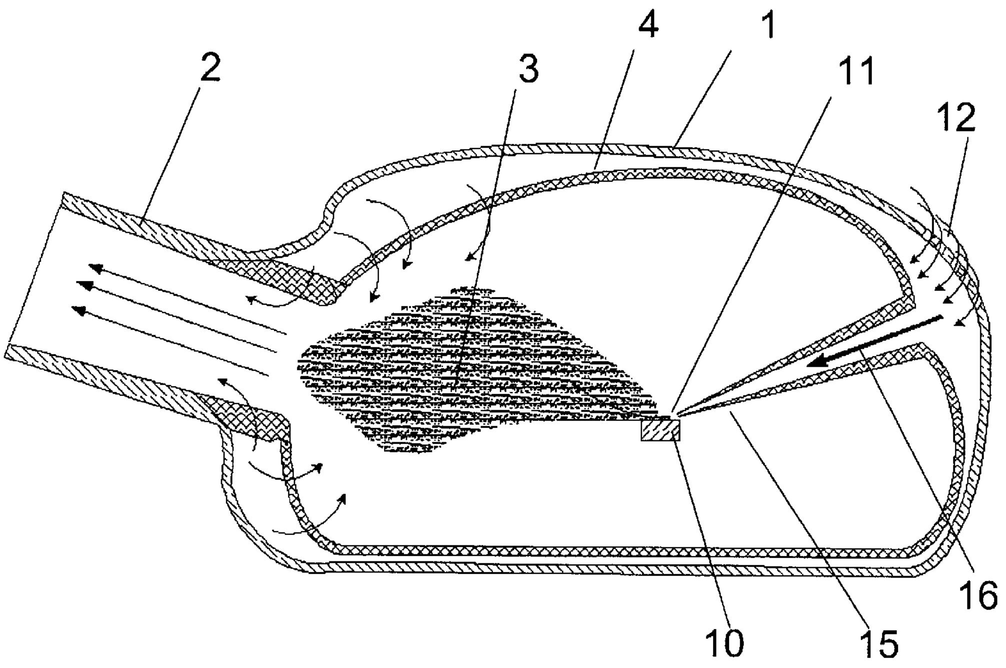
FIG. 1 indicates in a schematic way according to the present invention operation of an inhaler device using a fixed carrier member.

In FIG. 1 the basic principle of the method according to the present invention is schematically illustrated.

Figure 7:
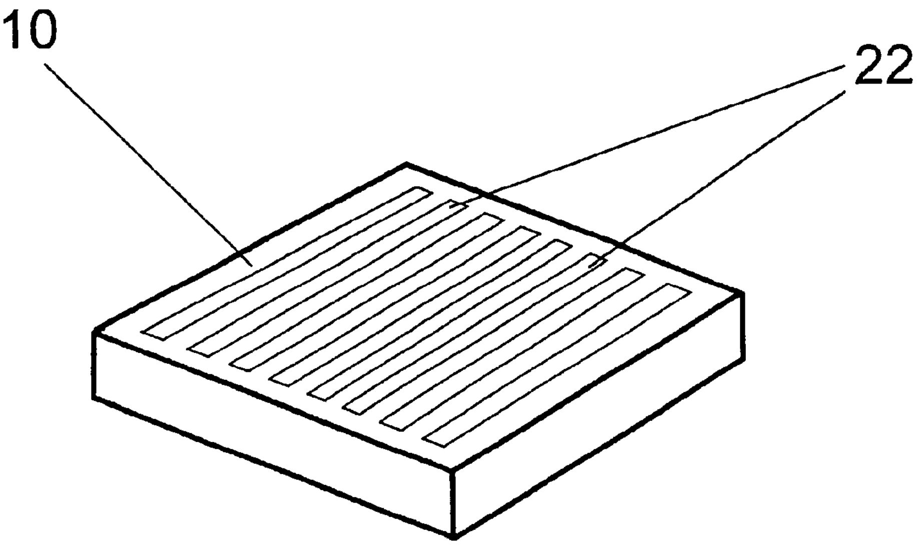
FIG. 7 illustrates an embodiment of a flat carrier disc for elongated strips forming doses of powder.
Figure 8:
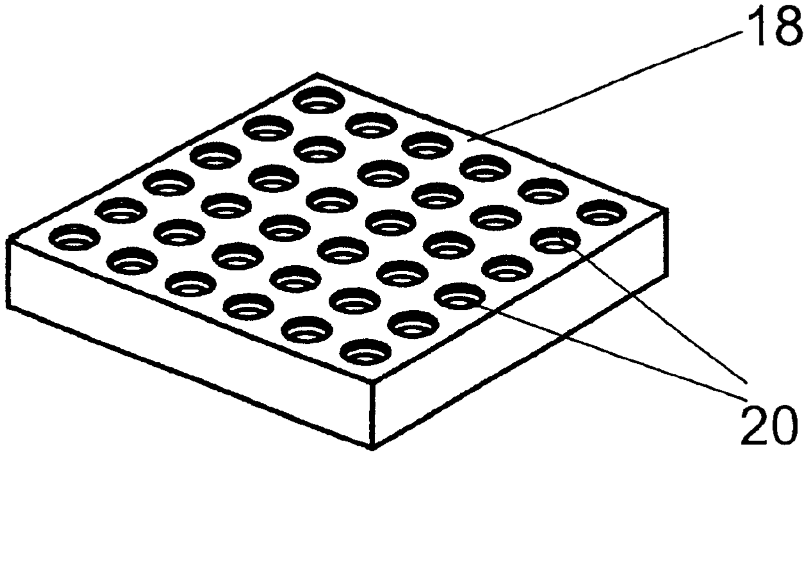
FIG. 8 illustrates an embodiment of a carrier disc for spots forming doses of powder.
Figure 9:
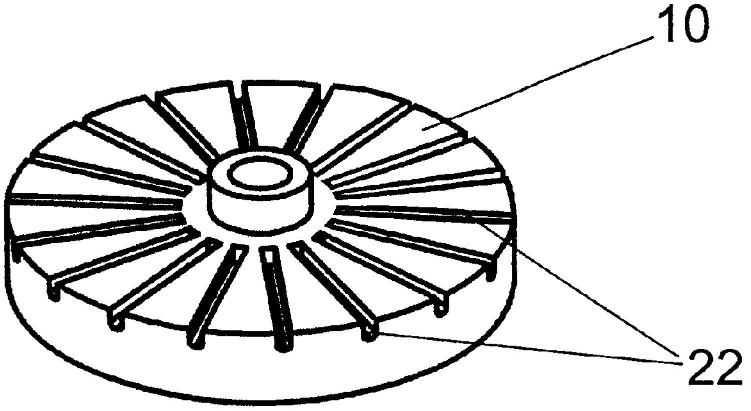
FIG. 9 illustrates another embodiment of a circular carrier disc presenting radial slots to receive strips of doses of powder.

An inhaler device is embodied by an illustrative casing 1 having a mouthpiece 2 for suction of the powder to be administered to the lungs of the user. A carrier 10 in advance prepared with a pre-metered electro-dose 11 of finely divided powder is positioned within the inhaler casing 1. In this context a pre-metered dose is defined either as a merged, elongated continuous amount of finely divided powder or as one or more separate, different spots of powder, in both cases deposited on a carrier member suitable for administration in a single inhalation. This carrier surface 10 in a basic embodiment is a flat fixed carrier provided with one or more pre-metered electro-doses 11. FIG. 7 shows an embodiment of a flat carrier 10 provided with strips of powder doses 22. FIG. 8 illustrates another embodiment of a flat carrier 18 provided with spots of powder doses 20. In the embodiment the spots are separated from each other by being placed in defined recesses, but they may also be placed directly onto the surface of the carrier. FIG. 9 illustrates still another embodiment of a flat carrier 10 in form of a circular disc with radial recesses 22 for powder doses. The powder to be dosed is preferably positioned as strips in such recesses to have a good separation between doses, but the powder may of course also be positioned as strips on an entirely flat carrier.

A pre-metered electro-dose here constitutes an active powder substance or a dry powder medical formulation, preferably an electro-powder, which is metered onto a device member forming a dose carrier, a metered dose having a fine particle fraction (FPF) presenting of the order 50% or more by mass of its content with a particle size below 5 $\mu$m, the dose further presenting an optimized porosity of 75 to 99,9%.

The electro-powder forms an active dry powder substance or dry powder medical formulation with a fine particle fraction (FPF) presenting of the order 50% or more of the powder by mass with an aerodynamic particle size below 5 $\mu$m and provides electrostatic properties with an absolute specific charge per unit mass after charging of the order 0.1 to 25 $\mu$C/g and presents a charge decay rate constant $Q_{50}$ of more than 0.1 s, and having a tap density of less than 0.8 g/ml and a water activity aw of less than 0.5.

In FIG. 1 an air jet 16 is directed to the electro-dose 11 of the carrier 10. This air jet blows the powder off from the carrier 10. In an illustrative embodiment a nozzle 15, positioned close to the dose of powder 11, forms the air jet 16. Generally a user-actuated release mechanism requires a certain well defined but adjustable minimum pressure differential between a surrounding atmosphere and the airways of an inhaling person. The user actuated release mechanism usually triggers off the dose delivery process by opening the interior of the inhaler for a directed air-stream. The air-stream is directed by means of a nozzle, which is designed such that it utilizes the available pressure drop caused by the inhalation to achieve a high air speed at the outlet near the dose to be delivered and with as little dissipative loss as possible in the process.

When the powder has been jetted off from the carrier 10, it will automatically be dispersed into the air above the carrier and the mixture 3 of air and powder will simultaneously be sucked out through a mouthpiece 2 of the inhaler casing 1. During this part of the inhalation, the inner part of the inhaler will act as a spacer, where the total dose will be spatially distributed in the air before coming into the mouthpiece 2.

To prevent powder from depositing onto the inner faces of the casing 1 which normally happens when spacers are used in inhalers of today, an additional active wall 4 is introduced. The principle of active walls is further disclosed in our Swedish Patent SE 9904484-4 (Swedish Publication No. SE 513 696). Through this wall a small portion of air will pass either directly from the ambient air if the active wall is a structural element of the inhaler casing, or indirectly from a space between the casing 1 of the inhaler device and an additional inner enclosure using active walls 4 when air is sucked out through the mouthpiece 2 of the inhaler device. By choosing the optimal pressure drops and materials in the design of the casing 1 and the active wall elements 4 optimal aerodynamic conditions are obtained to help perfect the resulting airflow. The inhaler is generally designed for a user induced pressure drop in the range 1–5 kPa resulting in an airflow of 15–50 l/min and a low air velocity through the mouthpiece to get highest possible amount of powder from the dose to the deep lungs.

Figure 6:
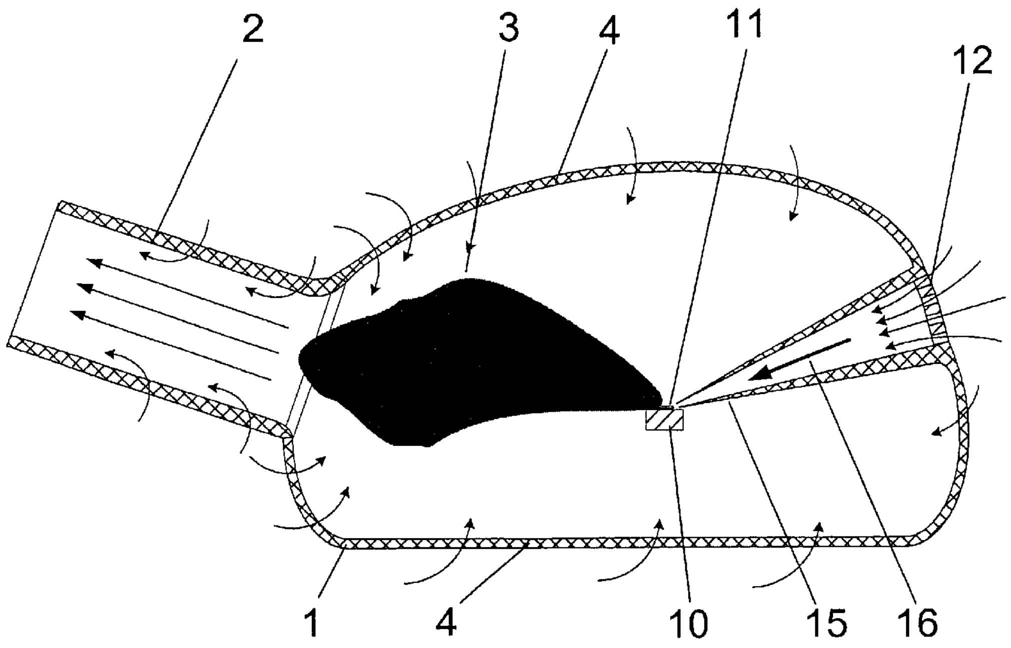
FIG. 6 illustrates in a sixth embodiment the inhaler device using a single porous supporting casing using active wall elements.

In another embodiment, schematically illustrated in FIG. 6, the inhaler casing 1 uses integrated active porous wall elements 4 at least partly as necessary to let small flows of air in through the casing wall to prevent powder from depositing onto the inner faces of the inhaler during an inhalation operation.

To jet off powder in this way from a carrier will consistently avoid the problems of powder sticking to the inner faces of for instance the mouthpiece where the speed of the air-powder mixture normally is very high and the concentration of powder is high.

Figure 2:
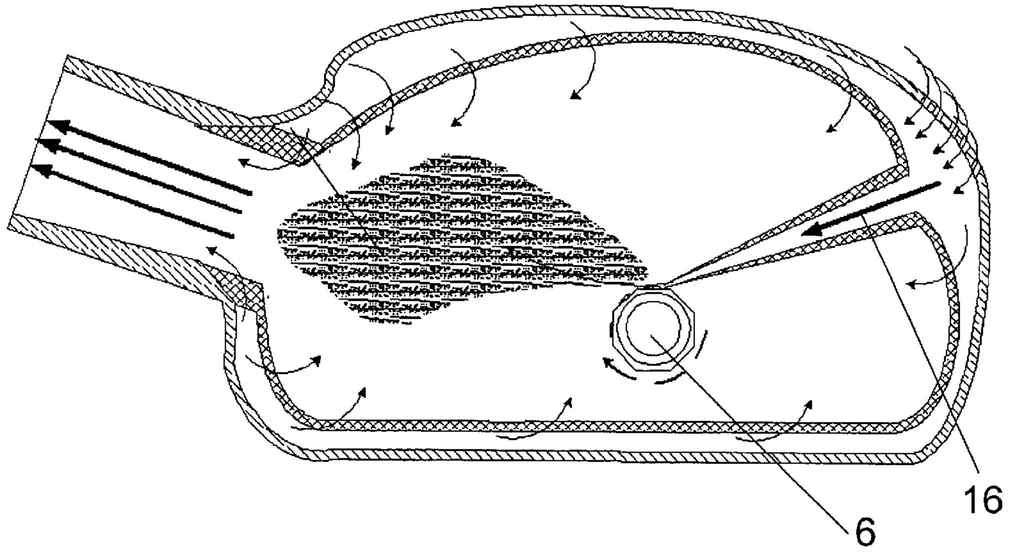
FIG. 2 illustrates in a second alternative, according to the present invention, operation of the inhaler device using a rotating cassette carrier.
Figure 10:
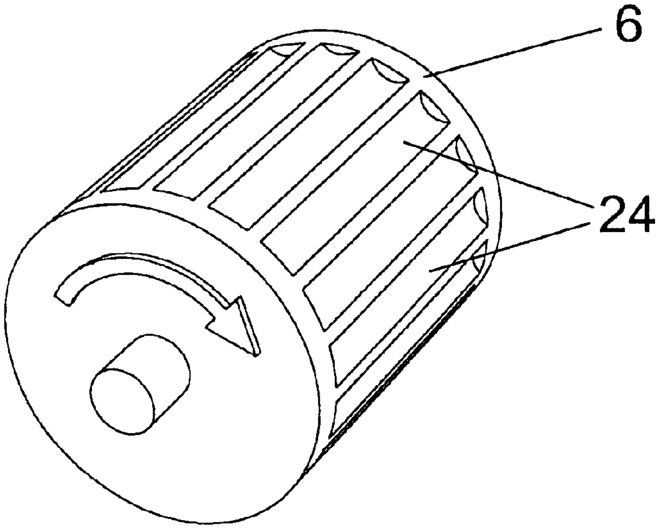
FIG. 10 illustrates an embodiment of a rotating cassette presenting elongated strips of powder doses.

In another embodiment in FIG. 2 a rotating cassette 6 replaces the flat carrier 10. The cassette 6 contains of the order of 4 to 20 electro-doses of powder and will move automatically by means of a suitable mechanical construction one step forward for each inhalation. The mechanical construction in a preferred embodiment will also include a member opening the sealed dose immediately before the inhalation. In this alternative, it is also possible to use a container with pressurized air combined with the cassette and to use a breath activated electrical motor to rotate the cassette 6. An embodiment of such a cassette 6 is further demonstrated in FIG. 10 illustrating positions for elongated strips of doses 24.

Figure 3:
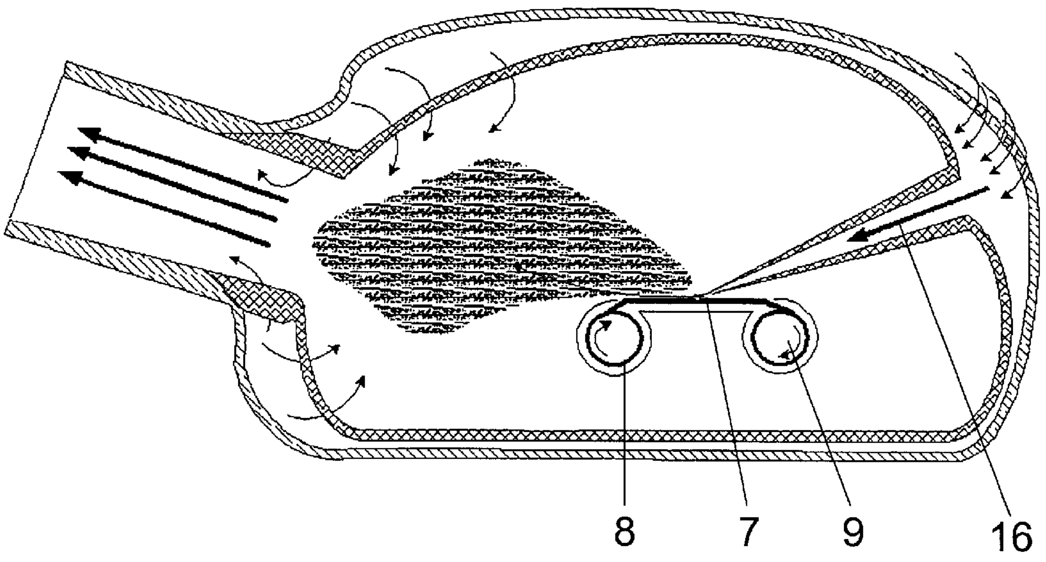
FIG. 3 illustrates in a third embodiment the operation of the inhaler device using a carrier in the form of a belt.

In a third embodiment in FIG. 3 the carrier may constitute a carrier belt 7 giving the possibility to load a big number of doses into the inhaler. The carrier belt has two rollers, one magazine roll 8 and one receiving roll 9. The belt is moving one step forward for each inhalation with the help of for instance an electrical motor connected to the receiving roll. Alternatively the belt is moving forward during the inhalation to get a continuous dosing of the powder.

Figure 4:
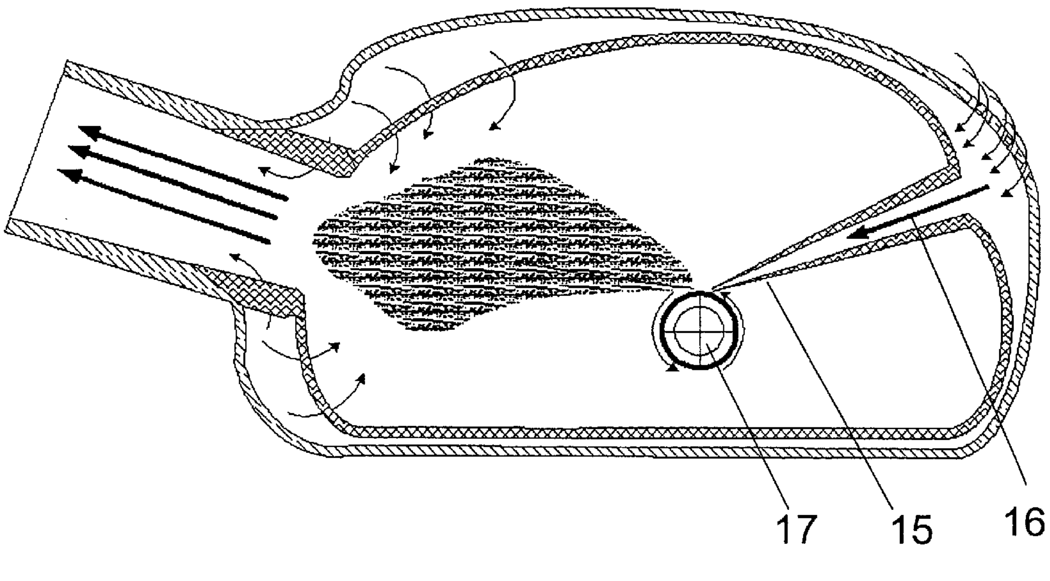
FIG. 4 illustrates in a fourth embodiment the operation of the inhaler device using a carrier in the form of a rotating cylinder.
Figure 11:
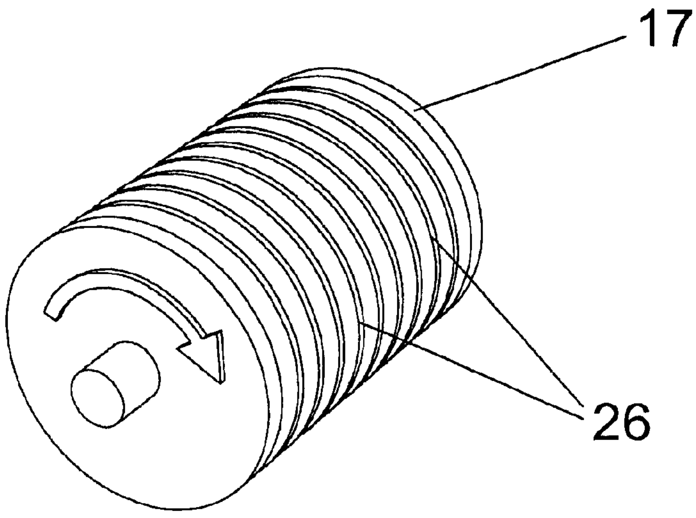
FIG. 11 illustrates another embodiment of a rotating cassette presenting circular elongated doses of powder.

In a fourth embodiment in FIG. 4 the powder is jetted off as a function of time in a controlled way by the nozzle 15 from a cylinder 17 provided with one or more spots or elongated strips of electro-powder. At the instance of an inhalation, the cylinder will in one alternative do one revolution and one dose is jetted off during a set time for an optimal inhalation. In FIG. 11 yet another embodiment of the rotating cassette 17 indicated in FIG. 4 is demonstrated. The cassette 17 in this embodiment presents circular elongated doses of powder 26. The inhaler then is automatically ready for next inhalation, as the air jet automatically will change to next strip. In another alternative, the powder strip can also be prepared in the form of a spiral on the surface of the cylinder, which will make it possible to change the delivered dose by choosing from part of a resolution to several revolutions of the cylinder. In addition, in this case the inhaler is immediately ready for next inhalation only by following the spiral strip. The flexibility with the cylinder will give the possibility to always get the correct dose mass and the optimal time for inhalation. A thin film to avoid moisture pickup will preferably protect the powder.

The release of powder by the air jet 16 will be activated by the inspiration of the user. The air jet 16 will be a direct effect of the outgoing air stream through the mouthpiece 2 or in another embodiment may be indirectly started by activation of an included small container with pressurized air. Such a container with pressurized air may simply be combined with the cylinder 6. It will also be possible to use a breath activated electrical motor to rotate the cylinder 17.

Figure 5:
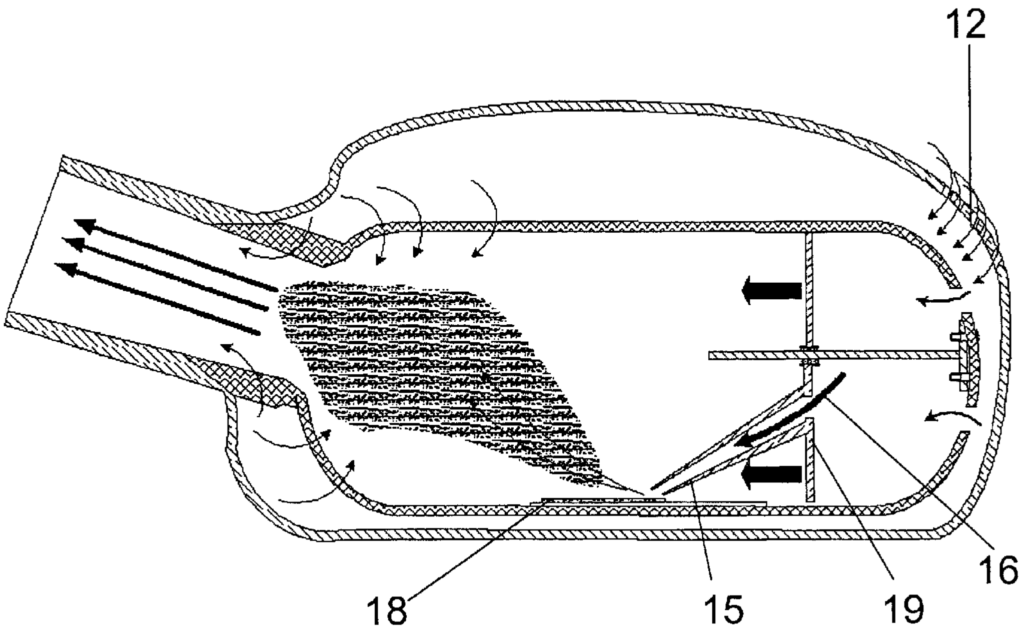
FIG. 5 illustrates in a fifth embodiment operation of the inhaler device using a moving air jet.

In a fifth embodiment in FIG. 5 a movable air jet 16, is used to blow a dose off a carrier provided with one or a number of electro-doses arranged as one or more spots or elongated strips to get a defined release of powder during an inhalation operation. The carrier can be in the form of a flat disc or a flat circular disc.

The electro-dose is jetted off in a controlled way by the nozzle 15 moving along the track of powder either by moving the nozzle as shown in FIG. 5 or moving the carrier in a linear motion. The amount of powder released per unit time will depend on two factors, the physical form of the dose and the relative movement between the nozzle and the carrier. In the first case, the moving nozzle is a part of a moving wall 19, which is pushed forward as shown by the arrows by the air coming in through openings 12 when the inhalation starts. In this way, the inhalation time can be optimized by a correct aerodynamic construction of the inhaler device. When moving the carrier of the other alternative the wall 19 is fixed and the carrier 18 with the electro-powder is moving. A breath-activated motor can alternatively perform the movements of the nozzle or the carrier and the use of pressurized air from a small breath-activated container can perform blowing off powder.

Figure 12:
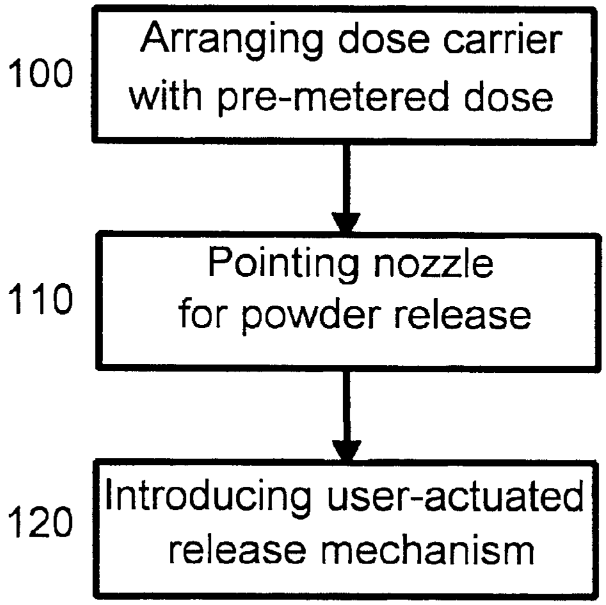
FIG. 12 is a flow diagram illustrating the method according to the present invention.

FIG. 12 presents a summary of the present method starting at a step 100. In step 100 a dose carrier is arranged with at least one pre-metered dose. In a succeeding step 110 a nozzle is pointed towards the dose onto the dose carrier for a release of powder. Finally in a step 120 a user-actuated release mechanism is introduced for initiating the release of powder from the dose carrier by means of the nozzle.

It will be obvious to a person skilled in the art that the present inhaler device may be modified and changed in many ways without departing from the scope of the present invention, which is defined by the appended claims

What is claimed is:

1. An inhaler comprising:

a particle distribution chamber defined by a wall, said wall being permeable to air and impermeable to particles in said particle distribution chamber;

a mouthpiece that opens into said particle distribution chamber and through which particles are withdrawn when air is withdrawn from said particle distribution chamber through said mouthpiece;

a carrier inside said particle distribution chamber, said carrier for carrying the particles that are to be withdrawn when air is drawn through said mouthpiece; and a jet inside said particle distribution chamber directed toward said carrier, wherein air is drawn through said wall into said particle distribution chamber to prevent particles from being deposited on said wall when air is drawn through said mouthpiece.

2. The inhaler of claim 1, further comprising an exterior covering that surrounds and is spaced from said wall, said exterior covering having an air passage therethrough.

3. The inhaler of claim 1, wherein said wall defines an exterior of the inhaler.

4. The inhaler of claim 1, wherein said carrier is spaced from said wall.

5. The inhaler of claim 1, wherein said carrier is directly on an interior surface of said wall.

6. The inhaler of claim 1, wherein said jet is an inwardly extended portion of said wall.

7. The inhaler of claim 6, wherein said inwardly extended portion is conic.

8. The inhaler of claim 1, wherein said carrier is a flat disc.

9. The inhaler of claim 1, wherein said carrier is a rotatable cylinder.

10. The inhaler of claim 1, wherein said carrier comprises a movable belt.

11. The inhaler of claim 1, wherein said carrier is a grooved disc.

12. A method of releasing particles from a carrier in an inhaler, the method comprising the steps of:

defining a particle distribution chamber with a wall that is permeable to air and impermeable to particles in the particle distribution chamber;

providing a mouthpiece that opens into the particle distribution chamber and through which particles are withdrawn when air is drawn through the mouthpiece;

placing the particles that are to be withdrawn through the mouthpiece on a carrier inside the particle distribution chamber; and directing a jet inside the particle distribution chamber toward the carrier, wherein air is drawn through the wall into the particle distribution chamber to prevent particles from being deposited on the wall when air is drawn through the mouthpiece.

* * * * *